United States Patent [19]
Buechler

[11] Patent Number: 6,037,455
[45] Date of Patent: *Mar. 14, 2000

[54] PROPOXYPHENE DERIVATIVES AND PROTEIN AND POLYPEPTIDE PROPOXYPHENE DERIVATIVE CONJUGATES AND LABELS

[75] Inventor: Kenneth F. Buechler, San Diego, Calif.

[73] Assignee: Biosite Diagnostics Incorporated, San Diego, Calif.

[ * ] Notice: This patent is subject to a terminal disclaimer.

[21] Appl. No.: 07/973,997

[22] Filed: Nov. 9, 1992

[51] Int. Cl.⁷ .......................... C07K 17/06; C07D 49/16; C07H 13/02; G01N 33/532

[52] U.S. Cl. .......................... 530/404; 530/405; 530/406; 530/408; 530/409; 562/476; 549/68; 568/589; 558/230; 560/147

[58] Field of Search .................................. 530/404, 405, 530/406, 408, 409; 562/426; 549/68; 568/589; 558/230; 560/147

[56] References Cited

U.S. PATENT DOCUMENTS

| | | | |
|---|---|---|---|
| 4,025,501 | 5/1977 | Leute | 530/363 |
| 4,067,774 | 1/1978 | Rubenstein et al. | 435/188 |
| 4,232,119 | 11/1980 | Carlsson et al. | 435/7.9 |
| 4,695,624 | 9/1987 | Marburg et al. | 530/395 |
| 5,233,042 | 8/1993 | Buechler | 546/129 |
| 5,237,057 | 8/1993 | Buechler et al. | 536/119 |
| 5,302,703 | 4/1994 | Buechler et al. | 530/404 |
| 5,302,715 | 4/1994 | Buechler et al. | 540/507 |
| 5,331,109 | 7/1994 | Buechler | 530/404 |
| 5,414,085 | 5/1995 | Buechler et al. | 544/300 |

FOREIGN PATENT DOCUMENTS 9218866 10/1992 WIPO .

OTHER PUBLICATIONS

Rowley et al (1975) J. Biol. Chemistry 150(10): 3759–3766.
Blair et al (1983) J. Immunol. Methods. 59: 129–143.
Jung et al (1981) Biochem. Biophys. Res. Commun. 101(2): 599–604.

*Primary Examiner*—Marian C. Knode
*Assistant Examiner*—Jay Williams
*Attorney, Agent, or Firm*—Lyon & Lyon LLP

[57] ABSTRACT

The present invention is directed to novel propoxyphene derivatives which are synthesized for the covalent attachment to antigens (proteins or polypeptides) for the preparation of antibodies or receptors to propoxyphene and propoxyphene metabolites. The resulting novel antigens may be used for the production of antibodies or receptors using standard methods. Once generated, the antibodies or receptors and the novel derivatives which are covalently attached to proteins, polypeptides or labels may be used in the immunoassay process.

6 Claims, 1 Drawing Sheet

PROPOXYPHENE DERIVATIVES AND PROTEIN AND POLYPEPTIDE PROPOXYPHENE DERIVATIVE CONJUGATES AND LABELS

FIELD OF THE INVENTION

This invention is in the field of ligand receptor assays, including immunoassays, for the detection of propoxyphene and selected metabolites of propoxyphene in a fluid sample. More particularly, this invention relates to methods for the synthesis of novel propoxyphene derivatives and protein and polypeptide propoxyphene derivative conjugates and labels for use in the preparation of antibodies to propoxyphene metabolites and for use in the immunoassay process.

BACKGROUND OF THE INVENTION d-Propoxyphene is a narcotic analgesic, but unlike morphine and codeine, it is much less addictive. However, because of its narcotic effect, propoxyphene has become a drug of abuse. Thus, the illicit and abusive use of propoxyphene has resulted in a medical need for antibodies and diagnostics to rapidly detect propoxyphene and propoxyphene metabolites in order to monitor and treat abuse.

The preparation of antibodies to propoxyphene and propoxyphene metabolites requires the synthesis of propoxyphene derivatives in order to covalently attach the derivative to an antigenic polypeptide or protein. In addition, the propoxyphene derivative is covalently attached to various polypeptides, proteins or labels for use in screening antibodies and in the immunoassay process. The propoxyphene derivative should mimic the structure of the propoxyphene metabolites sought to be measured. Therefore, the selection and synthesis of the types of propoxyphene derivatives for covalent attachment to proteins, polypeptides or labels is critical. In addition, the propoxyphene derivatives need to be stable and soluble in an aqueous solution.

SUMMARY OF THE INVENTION

The present invention is directed to novel propoxyphene derivatives which are synthesized for the covalent attachment to antigens (proteins or polypeptides) for the preparation of antibodies to the propoxyphene metabolites. The resulting novel antigens may be used for the production of antibodies using standard methods. Once generated, the antibodies and the novel derivatives which are covalently attached to proteins, polypeptides or labels may be used in the immunoassay process.

DEFINITIONS

In accordance with the present invention and as used herein, the following terms, are defined with the following meanings, unless explicitly stated otherwise.

"Drug" shall mean any compound or ligand which either as a result of spontaneous chemical reaction or by enzyme catalyzed or metabolic reaction, generates an intrinsic activity when administered to a biological system. The drug may be metabolized to a derivative of the drug by a biological system. Common examples of drugs and their metabolites are propoxyphene, morphine, barbiturates, tetrahydrocannabinol, phencyclidine, amphetamines, methamphetamines, opiates, benzodiazepines, cocaine, estrone-3-glucuronide, pregnanediol-glucuronide, cotinine, lysergic acid diethylamide, methadone, anabolic steroids, tricyclic anti-depressants.

"Drug derivative" shall mean a ligand derivative, drug, drug metabolite or a drug analogue conjugated to a linking group.

"Drug metabolite" shall mean a compound upstream or downstream from a drug in a biochemical or metabolic pathway, or an intermediate.

"Label" shall mean a signal development element or a means capable of generating a signal, for example, a dye or an enzyme. The attachment of a drug derivative to the label can be through covalent bonds, adsorption processes, hydrophobic and/or electrostatic bonds, as in chelates and the like, or combinations of these bonds and interactions.

"Binding domain" shall refer to the molecular structure associated with that portion of a receptor that binds ligand. More particularly, the binding domain may refer to a polypeptide, natural or synthetic, or nucleic acid encoding such a polypeptide, whose amino acid sequence represents a specific region of a protein, said domain, either alone or in combination with other domains, exhibiting binding characteristics which are the same or similar to those of a desired ligand/receptor binding pair. Neither the specific sequences nor the specific boundaries of such domains are critical, so long as binding activity is exhibited. Likewise, used in this context, binding characteristics necessarily includes a range of affinities, avidities and specificities, and combinations thereof, so long as binding activity is exhibited.

"Linking group" shall mean the "chemical arm" between the protein, polypeptide or label and a drug or drug derivative. As one skilled in the art will recognize, to accomplish the requisite chemical structure, each of the reactants must contain the necessary reactive groups. Representative combinations of such groups are amino with carboxyl to form amide linkages, or carboxy with hydroxy to form ester linkages or amino with alkyl halides to form alkylamino linkages, or thiols with thiols to form disulfides, or thiols with maleimides or alkylhalides to form thioethers. Obviously, hydroxyl, carboxyl, amino and other functionalities, where not present may be introduced by known methods. Likewise, as those skilled in the art will recognize, a wide variety of linking groups may be employed. The structure of the linkage should be a stable covalent linkage formed to attach the drug or drug derivative to the protein, polypeptide or label. In some cases the linking group may be designed to be either hydrophilic or hydrophobic in order to enhance the desired binding characteristics of the ligand and the receptor. The covalent linkages should be stable relative to the solution conditions under which the ligand and linking group are subjected. Generally preferred linking groups will be from 1–20 carbons and 0–10 heteroatoms (NH, O, S) and may be branched or straight chain. Without limiting the foregoing, it should be obvious to one skilled in the art that only combinations of atoms which are chemically compatible comprise the linking group. For example, amide, ester, thioether, thiol ester, keto, hydroxyl, carboxyl, ether groups in combinations with carbon-carbon bonds are acceptable examples of chemically compatible linking groups. Other chemically compatible compounds which may comprise the linking group are set forth in this Definition section and hereby are incorporated by reference.

"Hydrocarbyl" shall refer to an organic radical comprised of carbon chains to which hydrogen and other elements are attached. The term includes alkyl, alkenyl, alkynyl and aryl groups, groups which have a mixture of saturated and unsaturated bonds, carbocyclic rings and includes combinations of such groups. It may refer to straight-chain, branched-chain cyclic structures or combinations thereof.

"Aryl" shall refer to aromatic groups which have at least one ring having a conjugated pi electron system and includes carbocyclic aryl, heterocyclic aryl and biaryl groups, all of which may be optionally substituted.

"Carbocyclic aryl groups" shall refer to groups wherein the ring atoms on the aromatic ring are carbon atoms. Carbocyclic aryl groups include monocyclic carbocyclic aryl groups and optionally substituted naphthyl groups.

"Monocyclic carbocyclic aryl" shall refer to optionally substituted phenyl, being preferably phenyl or phenyl substituted by one to three substituents, such being advantageously lower alkyl, hydroxy, lower alkoxy, lower alkanoyloxy, halogen, cyano, trihalomethyl, lower acylamino, lower amino or lower alkoxycarbonyl.

"Optionally substituted naphthyl" shall refer to 1- or 2-naphthyl or 1- or 2-naphthyl preferably substituted by lower alkyl, lower alkoxy or halogen.

"Heterocyclic aryl groups" shall refer to groups having from 1 to 3 heteroatoms as ring atoms in the aromatic ring and the remainder of the ring atoms carbon atoms. Suitable heteroatoms include oxygen, sulfur, and nitrogen, and include furanyl, thienyl, pyridyl, pyrrolyl, N-lower alkyl pyrrolo, pyrimidyl, pyrazinyl, imidazolyl, and the like, all optionally substituted.

"Optionally substituted furanyl" shall refer to 2- or 3-furanyl or 2- or 3-furanyl preferably substituted by lower alkyl or halogen.

"Optionally substituted pyridyl" shall refer to 2-, 3- or 4-pyridyl or 2-, 3- or 4-pyridyl preferably substituted by lower alkyl or halogen.

"Optionally substituted thienyl" shall refer to 2- or 3-thienyl, or 2- or 3-thienyl preferably substituted by lower alkyl or halogen.

"Biaryl" shall refer to phenyl substituted by carbocyclic aryl or heterocyclic aryl as defined herein, ortho, meta or para to the point of attachment of the phenyl ring, advantageously para; biaryl is also represented as the —$C_6H_4$—Ar substituent where Ar is aryl.

"Aralkyl" shall refer to an alkyl group substituted with an aryl group. Suitable aralkyl groups include benzyl, picolyl, and the like, and may be optionally substituted.

"Lower" referred to herein in connection with organic radicals or compounds respectively defines such with up to and including 7, preferably up to and including 4 and advantageously one or two carbon atoms. Such groups may be straight chain or branched.

The terms (a) "alkyl amino" (b) "arylamino," and (c) "aralkylamino," respectively, shall refer to the groups —NRR' wherein respectively, (a) R is alkyl and R' is hydrogen or alkyl; (b) R is aryl and R' is hydrogen or aryl, and (c) R is aralkyl and R' is hydrogen or aralkyl.

The term "acyl" shall refer to hydrocarbyl—CO— or HCO—.

The terms "acylamino" refers to RCONCR)— and ($RCO_2N$— respectively, wherein each R is independently hydrogen or hydrocarbyl.

The term "hydrocarbyloxycarbonyloxy" shall refer to the group ROC(O)O— wherein R is hydrocarbyl.

The term "lower carboalkoxymethyl" or "lower hydrocarbyloxycarbonylmethyl" refers to hydrocarbyl—OC(O)$CH_2$— with the hydrocarbyl group containing ten or less carbon atoms.

The term "carbonyl" refers to —C(O)—.

The term "carboxamide" or "carboxamido" refers to —$CONR_2$ wherein each R is independently hydrogen or hydrocarbyl.

The term "lower hydrocarbyl" refers to any hydrocarbyl group of ten or less carbon atoms.

The term "alkyl" refers to saturated aliphatic groups including straight-chain, branched chain and cyclic groups.

The term "alkenyl" refers to unsaturated hydrocarbyl groups which contain at least one carbon-carbon double bond and includes straight-chain, branched-chain and cyclic groups.

The term "alkynyl" refers to unsaturated hydrocarbyl groups which contain at least one carbon-carbon triple bond and includes straight-chain, branched-chain and cyclic groups.

The term "hydrocarbyloxycarbonylamino" refers to a urethane, hydrocarbyl—O—CONR— wherein R is H or hydrocarbyl and wherein each hydrocarbyl is independently selected.

The term "di(hydrocarbyloxycarbonyl)amino" refers to (hydrocarbyl—O—CO)$_2$N— wherein each hydrocarbyl is independently selected.

The term "hydrocarbylamino" refers to —NRR' wherein R is hydrocarbyl and R' is independently selected hydrocarbyl or hydrogen.

The term "mercapto" refers to SH or a tautomeric form.

The term "methene" refers to

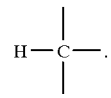

The term "methylene" refers to —$CH_2$—.

The term "alkylene" refers to a divalent straight chain or branched chain saturated aliphatic radical.

The term "oxy" refers to —O— (oxygen).

The term "thio" refers to —S— (sulfur).

"Disulfide" refers to —S—S—.

"Thiol ester" refers to

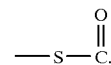

"Thioether" refers to C—S—C.

"Ester" refers to

"Analyte" shall mean substance of natural or synthetic origin sought to be detected and/or measured, said substance having a specific binding partner or receptor capable of a specific interaction with said analyte.

"Ligand" shall mean a binding partner to a ligand receptor. A substance which, if detected may be used to infer the presence of an analyte in a sample, including, without limitation, haptens, hormones, antigens, antibodies, deoxyribonucleic acid (DNA), ribonucleic acid (RNA), metabolites of the aforementioned materials and other substances of either natural or synthetic origin which may be of diagnostic interest and have a specific binding partner therefor, i.e., the ligand receptor of a ligand-receptor assay.

"Receptor" shall mean a receptor capable of binding ligand, typically an antibody, or a fragment thereof, but which may be another ligand, depending on assay design.

"Ligand-Receptor Assay" shall mean an assay for an analyte which may be detected by the formation of a complex between a ligand and a ligand receptor which is capable of a specific interaction with that ligand. Ligand-Receptor assays may be competitive or non-competitive, homogeneous or heterogeneous.

"Immunogen" shall mean a chemical or biochemical structure, determinant, antigen or portion thereof, which elicits an immune response, including, for example, polylysine, bovine serum albumin and keyhole limpet hemocyanin (KLH).

"Antigenic" shall mean a chemical or biochemical structure, determinant, antigen or portion thereof which is capable of inducing the formation of an antibody.

Figure 1:
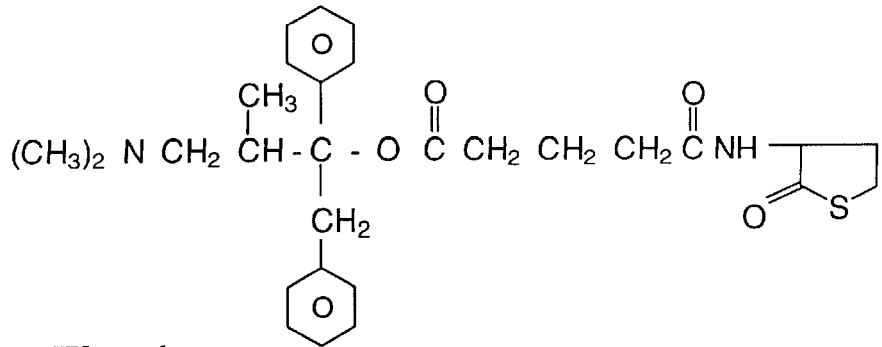
FIGS. 1 through 4 depict the structures of the compounds of Examples 2, 3, 5 and 6, respectively, namely.
Figure 2:
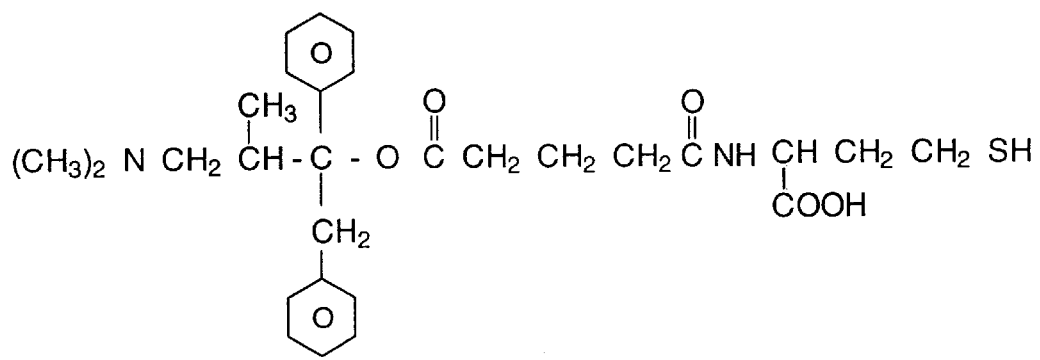
Figure 3:
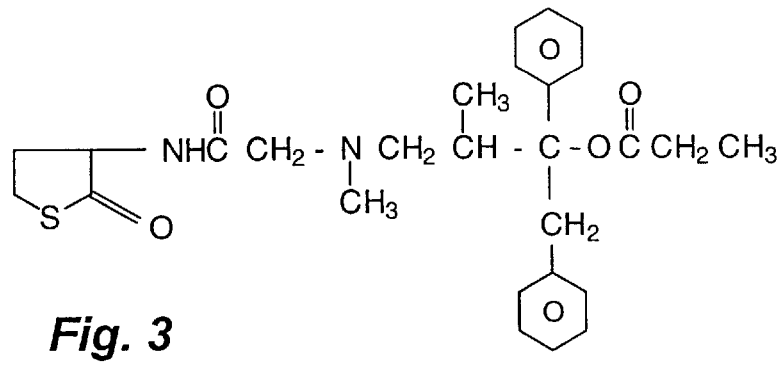
Figure 4:
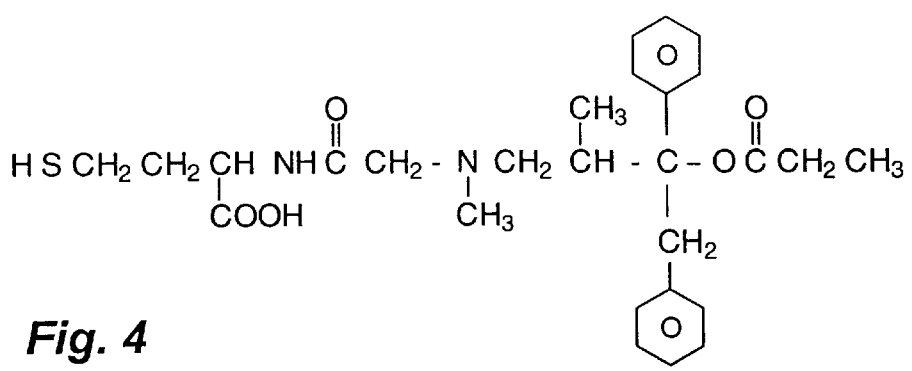

4-Dimethylamino-1,2-diphenyl-3-methyl-2-glutaroxy-(2-amino-4-thiolbutanoic acid thiolactone)-amide butane;

4-Dimethylamino-1,2-diphenyl-3-methyl-2-glutaroxy (cysteine) amide butane;

4-Methyl-4-[(2-amino-4-thio(butanoic acid thiolactone) acetamide]-1,2-diphenyl-3-methyl-2-propionoxybutane; and 4-Methyl-4-[(cysteine)acetamide]-1,2-diphenyl-3-methyl-2-propionoxybutane.

DETAILED DESCRIPTION OF THE PREFERRED EMBODIMENTS

Novel compounds are described which are used in the generation of antibodies and in the immunoassay process generally. The compounds are derivatives of propoxyphene and the propoxyphene metabolites. The elaboration of propoxyphene can be performed at either end of the propoxyphene molecule; that is, the ethyl ester group may be substituted with another aliphatic ester group which includes an amine, carboxylic acid or thiol function to aid in the attachment of the derivative to the protein, polypeptide or label. In addition, the opposite end of the propoxyphene molecule can be elaborated, for example, starting with norpropoxyphene and alkylating the secondary amine with a haloalkyl thiol ester or acylating with a carboxylic acid thiol ester. The synthesis of a particular derivative should allow for the character of the propoxyphene or propoxyphene metabolite derivative to be properly presented to the antibody or receptor in a manner which allows for the desired binding interaction. The synthesis of the linking group between the protein, polypeptide or label and the propoxyphene or propoxyphene metabolite derivative is designed to achieve the desired binding of the drug derivative and the receptor. For example, the derivative may be displaced from the surface of the protein, polypeptide or label to allow the derivative to present itself to the binding domain of receptors.

In general, the compounds of this invention have the following formula:

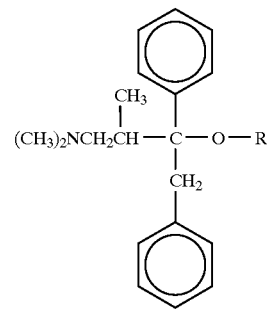

where R is a linking group comprising one of the following;

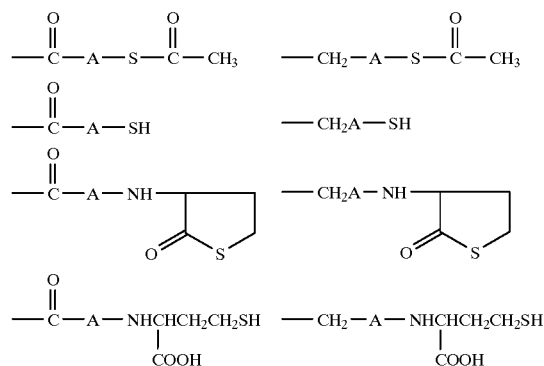

where A is a linking group of from 1 to 20 carbons and from 0 to 10 heteroatoms (NH, O, S), either branched or straight chain.

In addition, the general form of the immunogenic protein or polypeptide molecule or the protein or polypeptide molecule or label derivatized via an amide, disulfide, thioether, or ester bond to the molecule or label to a compound of the formula is of the following:

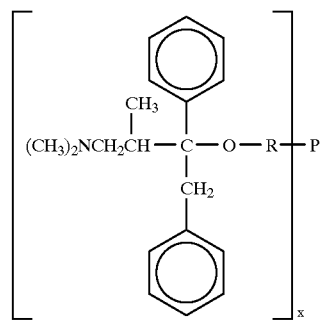

where P is an antigenic protein or polypeptide or a protein, polypeptide or label;

where x is at least one and not greater than 100;

where R is a linking group comprising one of the following:

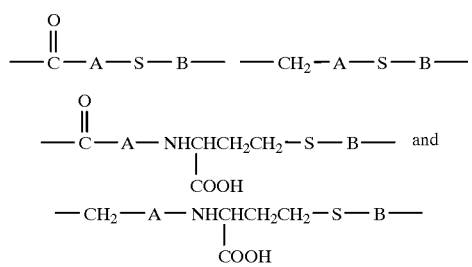

where A is a linking group of from 1 to 20 carbons and 0 to 10 heteroatoms (NH, O, S) either branched or straight chain;

where B is a linking group ultimately attached to a protein, polypeptide or label selected from the group comprising:

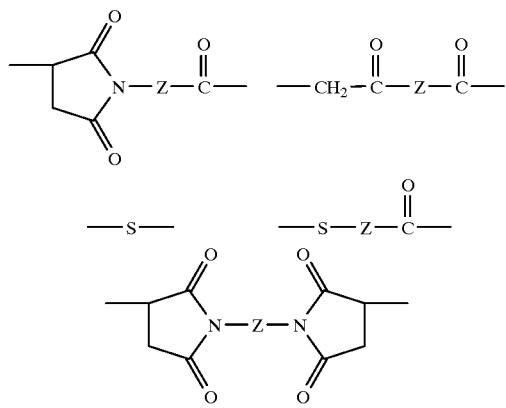

where Z is a linking group of from 1 to 20 carbons and 0 to 10 heteroatoms (NH, O, S) and may be branched or straight chain.

In general, the compounds of this invention also have the following formula:

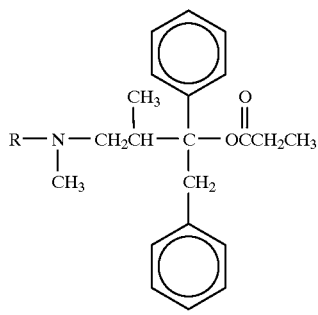

where R is a linking group comprising one of the following

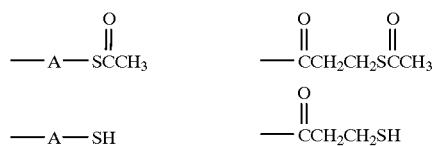

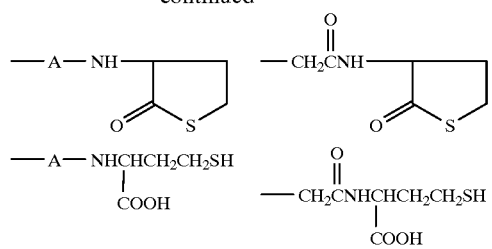

where A is a linking group of from 1 to 20 carbons and from 0 to 10 heteroatoms (NH, O, S), either branched or straight chain.

In addition, the general form of the immunogenic protein or polypeptide molecule or the protein or polypeptide molecule or label which is derivatized via an amide, disulfide, thioether, or ester bond to the molecule or label to a compound of the formula is also of the following:

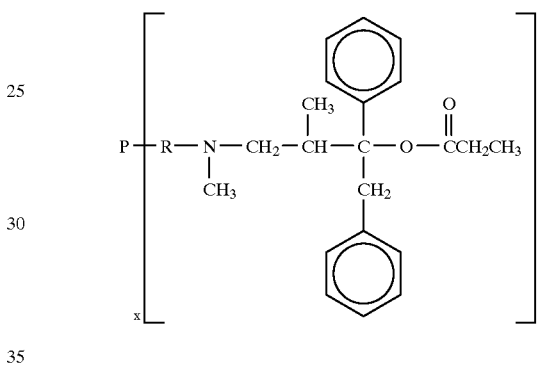

where P is an antigenic protein or polypeptide or a protein, polypeptide, or label;

where X is at least one and not greater than 100;

where R is a linking group of the following:

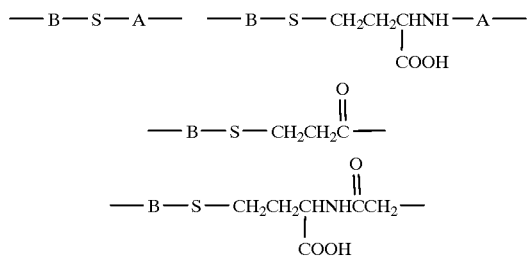

where A is a linking group of from 1 to 20 carbons and 0 to 10 heteroatoms (NH, O, S), either branched or straight chain;

where B is a linking group ultimately attached to a protein, polypeptide, or label selected from the group comprising:

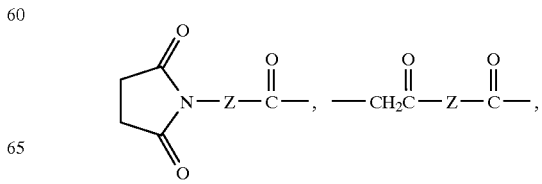

-continued

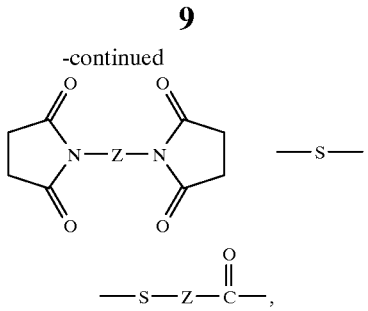

where Z is a linking group of from 1 to 20 carbons and 0 to 10 heteroatoms (NH, O, S) and may be branched or straight chain. The preferred (best mode) compounds of this invention have the following formula:

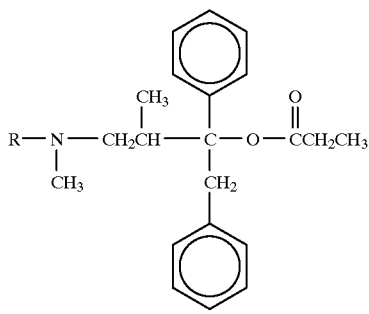

where R is a linking group comprising one of the following:

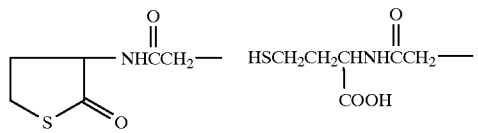

In addition, the preferred (best mode) immunogenic protein or polypeptide molecule or the protein or polypeptide molecule or label which is derivatized via an amide or ester bond to the molecule or label to a compound of the formula is of the following:

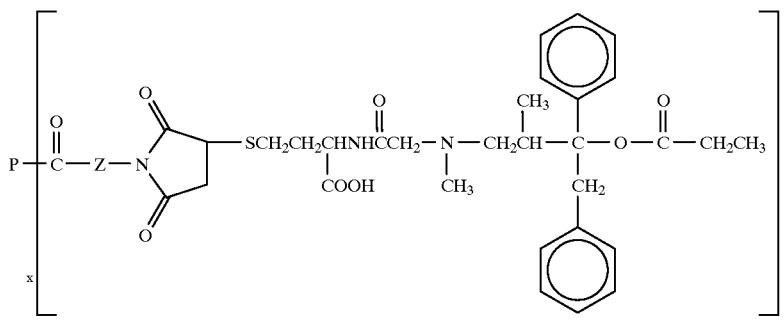

where P is an antigenic protein or polypeptide or a protein, polypeptide or label;
where x is at least one and not greater than 100;
where Z is a linking group of from 1 to 20 carbons and 0 to 10 heteroatoms (NH, O, S) and may be branched or straight chain.

Of particular interest are propoxyphene derivatives which have been synthesized by substitution of the ethyl ester group of propoxyphene with a linking group containing a thiol ester function. The linking group substituting the ethyl ester may be linked to the molecule by an ester or an ether function. The ester function can be prepared by reaction of the secondary alcohol of 4-dimethylamino-1,2-diphenyl-3-methyl-2-butanol with, for example, succinic anhydride or glutaric anhydride and the resulting carboxylic acid may be reacted with an amino alkyl thiol ester to form the thiol ester derivative of propoxyphene. The secondary alcohol may also be reacted with, for example, 2-bromo acetic acid to form an ether linkage rather an ester linkage. The ether linkage can be used if a more stable (for example, to hydrolysis in an aqueous solution) linkage is required. The resulting carboxylic acid may then be reacted with an amino alkyl thiol ester as previously described.

Propoxyphene derivatives can also be synthesized by alkylation or acylation of the secondary amine of norpropoxyphene. The alkylation reactions can be performed using various chain length alkyl halide carboxylic acids, for example 3-iodopropionic acid, to form an N-alkylated carboxylic acid propoxyphene derivative, which can then be further reacted with an amino alkyl thiol ester, such as homocysteine thiolactone, to synthesize the thiol ester derivative of the propoxyphene. The acylation reactions can be performed with various chain length alkyl thiol ester carboxylic acids, for example, 3-acetylthiopropionic acid to synthesize the thiol ester derivative of propoxyphene. The thiol esters of the resulting propoxyphene derivatives are hydrolyzed in dilute base, for example, 0.01 M potassium hydroxide, to generate the thiol group which is reacted with the thiol reactive group, such as a maleimide, an alkyl halide or a thiol. Those skilled in the art can recognize the versatility of synthetic strategies described herein.

The compounds are synthesized as thiols or thiol esters so that their covalent attachment to proteins, polypeptides or labels can easily be performed under mild conditions, for example, pH 7 in a protein solution. The protein, polypeptide or label is reacted with a reagent which incorporates a maleimide or alkylhalide into the molecule. These reagents and methods for their use are available from Pierce, Rockford, Ill., for example, for incorporation of maleimide groups onto proteins, polypeptides or labels one can use succinimidyl 4-(N-maleimidomethyl)cyclohexane-1-carboxylate (SMCC), succinimidyl 4-(p-maleimidophenyl) butyrate (SMPB) or m-maleimidobenzoyl-N-hydroxysuccinimide ester (MBS). For introduction of an alkyl halide into a protein, polypeptide or label one can use N-succinimidyl(4-iodoacetyl)aminobenzoate (SIAB) also from Pierce. The thiol reactive group, such as maleimide, an alkyl halide or a thiol can be incorporated into the protein, polypeptide or label prior to reaction with the drug thiol but the drug thiol can also be reacted with the thiol reactive compound prior to reaction with the protein, polypeptide or label. Also, bis-maleimide compounds of varying length can be reacted with thiol containing proteins, polypeptides or labels for covalent coupling of the propoxyphene derivatives. Conversely, the bis-maleimide compound can be reacted with the thiol derivative and subsequently to the thiol containing protein, polypeptide or label. Common bis-maleimides are bis-maleimidohexane from Pierce, N,N'-bis(3-maleimidopropionyl)-2-hydroxy-1,3-propanediamine from Sigma Chemical Co., St. Louis, Mo., and 1,1'-(methylenedi- 4,1-phenylene)-bismaleimide from Aldrich Chem. Co., Milwaukee, Wis. The thiol propoxyphene derivatives can also form disulfides with thiol containing polypeptide, protein or label molecules as a means to incorporate the derivative into the molecule.

The use of drug derivatives, immunogens and protein and polypeptide conjugates for generating antibodies and for use in the immunoassay process is described, for example, in U.S. Pat. Nos. 4,067,774, 4,952,336, 5,028,535 and 5,089,391.

EXPERIMENTAL EXAMPLES

Example 1

Synthesis of 4-Dimethylamino-1,2-diphenyl-3-methyl-2-glutaroxybutane (Propoxyphene glutarate)

(2S,3R)-(+)-4-Dimethylamino-1,2-diphenyl-3-methyl-2-butanol (5.0 g, $1.8 \times 10^{-2}$ mol) was dissolved in anhydrous pyridine (18 ml) and glutaric anhydride (12.0 g, $1.0 \times 10^{-1}$ mol) was added in one portion. The reaction mixture was stirred at 40° C. for 7 days. The solvent was removed in vacuo and the residue was dissolved in water (100 ml). The aqueous solution was washed 4 times with diethyl ether (100 ml) and made basic to pH 9 with potassium hydroxide solution (10N). The basic solution was washed 3 times with ethyl acetate (100 ml) and acidified with hydrochloric acid (6N) to pH 1.0. The acidic solution was extracted 4 times with chloroform (100 ml), dried over anhydrous magnesium sulfate and filtered. The chloroform was removed in vacuo and the residue was redissolved in water (100 ml). The water was removed in vacuo and the residue was dried in vacuo to yield 3.0 g (40%) of the title product as a beige crystalline solid: mp 199–201° C.

Example 2

Synthesis of 4-Dimethylamino-1,2-diphenyl-3-methyl-2-glutaroxy-(2-amino-4-thiolbutanoic acid thiolactone)-amide butane (Propoxyphene Glutarate HCTL)

Propoxyphene glutarate (0.2 g, $4.6 \times 10^{-4}$ mol), dl-homocysteine thiolactone HCTL hydrochloride (0.071 g, $4.6 \times 10^{-4}$ mol), and pyridine (0.17 ml, $2.0 \times 10^{-3}$ mol) were dissolved in anhydrous dimethyformamide (4.6 ml). 1-(3-Dimethylaminopropyl)-3-ethylcarbodiimide hydrochloride (0.98 g, $5.0 \times 10^{-4}$ mol) was added and the solution was stirred under argon at room temperature for 4 h. The solvent was removed in vacuo, the residue was dissolved in water (5.0 ml) and the solution was acidified with hydrochloric acid (1N) to pH 1. The water was removed in vacuo. The crude product was dissolved in 20 mM potassium phosphate, pH 4.60, (2.7 ml) and was purified on a Vydac 1×25 cm, reversed phase C18 column equilibrated in 20 mM potassium phosphate, pH 4.60, using a linear gradient of up to 100% methanol in 52 min at a flow rate of 2.0 ml/min. The product eluted between 34–36 min and the fractions were combined and the solvent was removed in vacuo. The white residue was triturated with methanol (20 ml) and filtered. The methanol was removed in vacuo to yield 0.06 g of the title compound.

Example 3

Synthesis of 4-Dimethylamino-1,2-diphenyl-3-methyl-2-glutaroxy(cysteine)amide butane Propoxyphene glutarate HCTL (16.2 mg, $3 \times 10^{-5}$ mol) was dissolved in 1.5 ml dimethylformamide/water (70/30, v/v). Potassium hydroxide (0.1 ml, 1N) was added and the solution sat at room temperature for 5 min. Potassium phosphate buffer (0.3 ml, 0.5 M, pH 7), was immediately added and the solution was adjusted to pH 7–7.5 with hydrochloric acid (1N). The title compound in solution was used as is to react with thiol reactive groups, such as maleimides, alkyl halides, or thiols, which are either free in solution or are coupled to proteins, polypeptides, or labels.

Example 4

Synthesis of 2(2-amino-4-thiolbutanoic acid Thiolactone) bromoacetamide (bromoacetyl-HCTL)

Bromoacetic acid (1.0 g, $7.2 \times 10^{-3}$ mol), dl-homocysteine thiolactome hydrochloride (1.1 g, $7.2 \times 10^{-3}$ mol) and pyridine (1.2 ml, $1.5 \times 10^{-2}$ mol) were dissolved in anhydrous dimethylformamide (36 ml) and then 1-(3-dimethylaminopropyl)-3-ethylcarbodiimide hydrochloride (1.52 g, $7.9 \times 10^{-3}$ mol) was added. The reaction was stirred at room temperature for 18 h. The solvents were removed in vacuo and ethanol (10 ml) was added to dissolve the residue and then the ethanol was removed in vacuo. Ethanol (10 ml) was again added to dissolve the residue and was removed in vacuo. Water (20 ml) was added to the oil and the aqueous solution was extracted 3 times with methylene chloride (45 ml). The combined organic extracts were dried over anhydrous magnesium sulfate. The solution was filtered and the solvent was removed in vacuo to give a clear oil. Diethyl ether (5 ml) was added and the resulting precipitate was collected and washed on a fritted funnel. The precipitate was dried in vacuo and 1.0 g of the title compound was recovered.

Example 5

Synthesis of 4-Methyl-4-[(2-amino-4-thiolbutanoic acid thiolactone)acetamide]-1,2-diphenyl-3-methyl-2-propionoxybutane (N-HCTL-Propoxyphene)

d-Norpropoxyphene maleate (88 mg, $2 \times 10^{-4}$ mol), bromoacetyl HCTL (48 mg, $2 \times 10^{-4}$ mol) and potassium carbonate (83 mg, $6 \times 10^{-4}$ mol) were dissolved in 2 ml dimethyformamide. The solution was stirred at room temperature for 24 h. The solvent was removed in vacuo and 0.5 M potassium phosphate, pH 7 (5 ml) was added to the residue. The aqueous suspension was extracted twice with ethyl acetate (5 ml) and the combined organic layers were washed with water (5 ml), dried with anhydrous magnesium sulfate, filtered and evaporated in vacuo. The residue was dissolved in ethyl ether (10 ml) and the solution was acidified with ethereal hydrochloric acid. The title compound precipitated as a white solid and was collected by filtration. The product was dried in vacuo and 73 mg was recovered.

Example 6

Synthesis of 4-Methyl-4-[(cysteine)acetamide]-1,2-diphenyl-3-methyl-2-propionoxybutane N-HCTL-propoxyphene (17.7 mg, $3.4 \times 10^{-5}$ mol) was dissolved in 1.6 ml dimethylformamide/water (70/30, v/v). Potassium hydroxide (0.1 ml, 1N) was added and the solution sat at room temperature for 5 min. Potassium phosphate buffer (0.3 ml, 0.5 M, pH 7) was immediately added and the solution was adjusted to pH 7–7.5 with hydrochloric acid (1N). The title compound in solution was used as is to react with thiol reactive groups, such as maleimides, alkyl halides, or thiols, which are either free in solution or are coupled to proteins, polypeptides, or labels.

Other embodiments are within the following claims.

I claim:

1. A Compound of the formula:

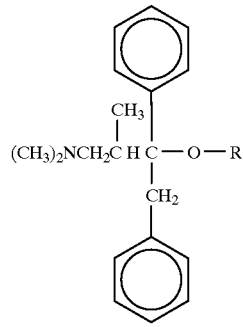

where R is a linking group selected from the group consisting of:

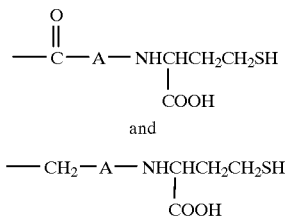

where A is a linking hydrocarbyl group of from 1 to 20 carbons and from 0 to 10 heteroatoms selected form the group consisting of nitrogen, oxygen, and sulfur, which may either be in the chain or substituted on the chain which may be straight or branched.

2. An immunogenic protein or polypeptide molecule or a protein or polypeptide molecule or a label derivatized to a compound of the formula:

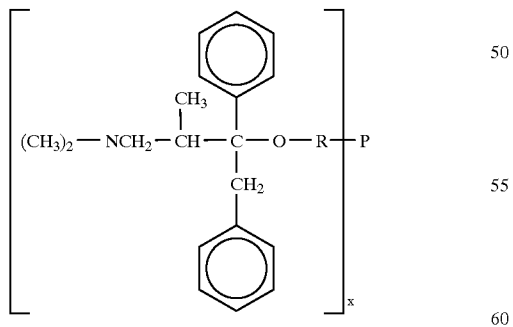

where P is an antigenic protein or polypeptide or a protein, polypeptide or label;

where x is at least one and not greater than 100;

where R is a linking group selected from the group consisting of:

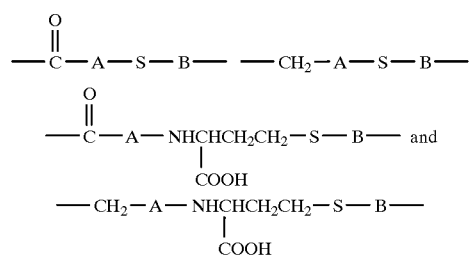

where A is a linking hydrocarbyl group from 1 to 20 carbons and 1 to 10 heteroatoms selected from the group consisting of nitrogen, oxygen, and sulfur, which may either be in the chain or substituted on the chain which may be straight or branched;

where B is a linking group ultimately attached to a protein, polypeptide or label selected from the group consisting of:

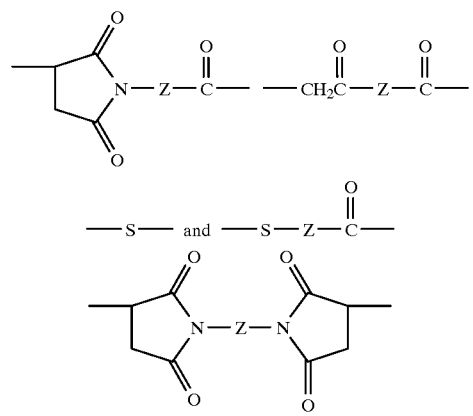

where Z is a linking hydrocarbyl group from 1 to 20 carbons and 0 to 10 heteroatoms selected from the group consisting of nitrogen, oxygen, and sulfur, which may either be in the chain or substituted on the chain which may be straight or branched.

3. A Compound of the formula:

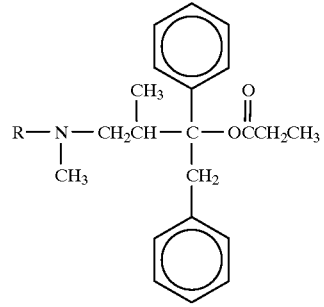

where R is a linking group selected from the group consisting of:

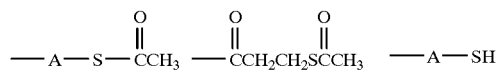

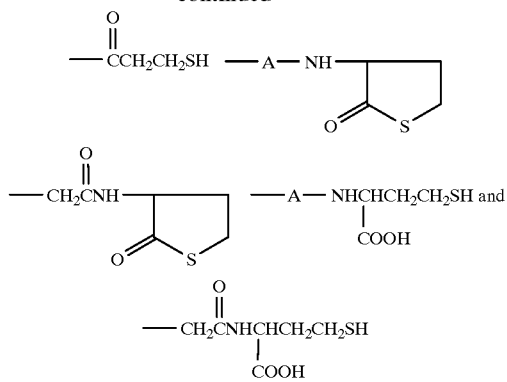

where A is a linking hydrocarbyl group of from 1 to 20 carbons and from 0 to 10 heteroatoms selected from the group consisting of nitrogen, oxygen, and sulfur, which may either be in the chain or substituted on the chain which may be straight or branched.

4. An immunogenic protein or polypeptide molecule or a protein or polypeptide molecule or a label derivatized to a compound of the formula:

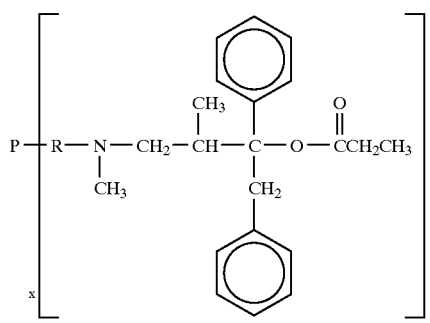

where P is an antigenic protein or polypeptide or a protein, polypeptide or label;
where x is at least on and not greater than 100;
where R is a linking group selected from the group consisting of:

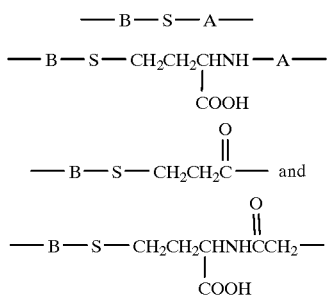

where A is a linking hydrocarbyl group of from 1 to 20 carbons and 0 to 10 heteroatoms selected from the group consisting of nitrogen, oxygen, and sulfur, which may either be in the chain or substituted on the chain which may be straight or branched;

where B is a linking group ultimately attached to a protein polypeptide or label selected from the group consisting of:

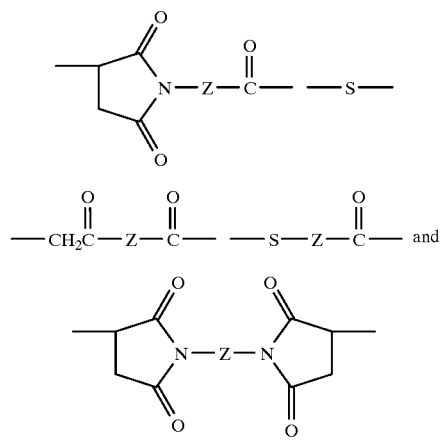

where Z is a linking hydrocarbyl group of from 1 to 20 carbons and from 1 to 10 heteroatoms selected from the group consisting of nitrogen, oxygen, and sulfur, which may either be in the chain or substituted on the chain which may be straight or branched.

5. A Compound of the formula:

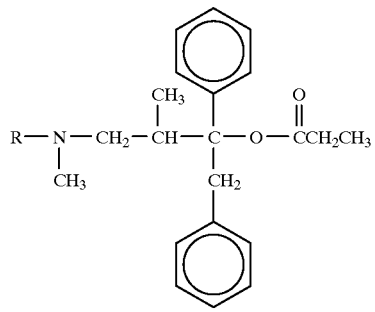

where R is a linking group selected from the group consisting of:

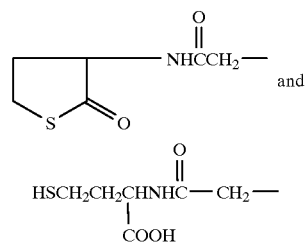

6. An immunogenic protein or polypeptide molecule or a protein or polypeptide molecule or label derivatized to a compound of the formula:

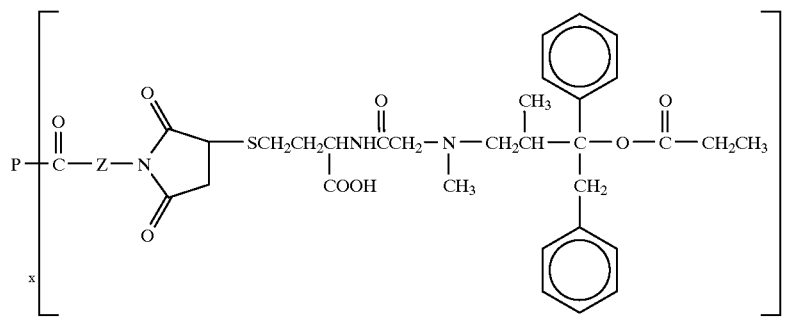
15
where P is an antigenic protein or polypeptide or a protein, polypeptide or label;
where x is at least one and not greater than 100;
where Z is a hydrocarbyl group of from 1 to 20 carbons and 0 to 10 heteroatoms selected from the group consisting of nitrogen, oxygen, and sulfur, which may either be in the chain or substituted on the chain which may be straight or branched.
* * * * *

UNITED STATES PATENT AND TRADEMARK OFFICE
CERTIFICATE OF CORRECTION

PATENT NO. : 6,037,455
DATED : March 14, 2000
INVENTOR(S) : Buechler

It is certified that error appears in the above-identified patent and that said Letters Patent is hereby corrected as shown below:

Column 17,
Line 19, "a hydrocarbyl" should read -- a linking hydrocarbyl --

Signed and Sealed this

Ninth Day of October, 2001

Attest:

*Nicholas P. Godici*

NICHOLAS P. GODICI
*Attesting Officer*      *Acting Director of the United States Patent and Trademark Office*